(12) United States Patent
Averbach et al.

(10) Patent No.: US 10,803,985 B2
(45) Date of Patent: Oct. 13, 2020

(54) METHOD OF FACILITATING IMAGING STUDY INTERPRETATIONS BETWEEN HEALTHCARE FACILITIES AND PHYSICIANS

(71) Applicant: MDWeb, LLC, New York, NY (US)

(72) Inventors: Michael Averbach, Forest Hills, NY (US); Sergey Fradkov, Edgewater, NJ (US); Michael Yuz, Ft Lauderdale, FL (US); Edward Kantor, Brooklyn, NY (US); Aleksandr Krakopolsky, Warminster, PA (US)

(73) Assignee: MDWEB, LLC

( * ) Notice: Subject to any disclaimer, the term of this patent is extended or adjusted under 35 U.S.C. 154(b) by 0 days.

(21) Appl. No.: 16/171,985

(22) Filed: Oct. 26, 2018

(65) Prior Publication Data

US 2020/0135326 A1   Apr. 30, 2020

(51) Int. Cl.
| | | |
|---|---|---|
| *G16H 30/20* | (2018.01) | |
| *G06Q 20/08* | (2012.01) | |
| *G16H 80/00* | (2018.01) | |
| *H04L 9/32* | (2006.01) | |
| *G06Q 20/36* | (2012.01) | |

(52) U.S. Cl.
CPC ......... *G16H 30/20* (2018.01); *G06Q 20/0855* (2013.01); *G06Q 20/3678* (2013.01); *G16H 80/00* (2018.01); *H04L 9/3213* (2013.01)

(58) Field of Classification Search
USPC ....................................................... 705/2–4
See application file for complete search history.

(56) References Cited

U.S. PATENT DOCUMENTS

| | | | | |
|---|---|---|---|---|
| 8,548,426 | B2 * | 10/2013 | Smith | G06Q 20/32 |
| | | | | 370/310.2 |
| 8,724,867 | B2 * | 5/2014 | Koff | G06F 19/321 |
| | | | | 382/128 |

(Continued)

OTHER PUBLICATIONS

Zhang, Peng, et al. "Blockchain technology use cases in healthcare." Advances in computers. vol. 111. Elsevier, 2018. 1-41.; available online at https://healthcare.report/Resources/Whitepapers/946ece8c-e671-4452-b068-5e8c38b2b1ca_blockchain-bookchapter-2018.pdf on Apr. 30, 2018.*

*Primary Examiner* — Mark Holcomb
(74) *Attorney, Agent, or Firm* — Burr & Forman LLP; Jeffrey H. Kamenetsky

(57) ABSTRACT

A method for facilitating selection, by a healthcare facility, of a physician from a plurality of physicians to provide interpretation of an imaging study, is provided. The method includes receiving physician credentials from at least one physician, receiving, from the healthcare facility, an imaging study and a request for interpretation of the imaging study, the request including physician selection criteria, providing access to the imaging study and the request for interpretation to qualified physicians whose credentials match the physician selection criteria, receiving an interpretation of the imaging study from those qualified physicians that have accepted the request for interpretation, comparing the physician credentials to the physician selection criteria, and selecting an imaging study interpretation from the received imaging study interpretations based on the comparing of the physician credentials to the physician selection criteria.

28 Claims, 6 Drawing Sheets

(56) References Cited

U.S. PATENT DOCUMENTS

| | | | | |
|---|---|---|---|---|
| 10,095,888 B1* | 10/2018 | Lee | ............ | G06F 21/64 |
| 2004/0122702 A1* | 6/2004 | Sabol | ............ | G06Q 50/22 |
| | | | | 705/2 |
| 2006/0031093 A1* | 2/2006 | Serrano | ............ | G06F 19/321 |
| | | | | 705/2 |
| 2007/0162305 A1* | 7/2007 | Miller | ............ | G06Q 10/00 |
| | | | | 705/2 |
| 2008/0140445 A1* | 6/2008 | Wang | ............ | G06Q 30/02 |
| | | | | 705/2 |
| 2008/0243539 A1* | 10/2008 | Barish | ............ | G06F 19/321 |
| | | | | 705/2 |
| 2011/0145933 A1* | 6/2011 | Gambhir | ............ | G06F 9/547 |
| | | | | 726/30 |
| 2012/0116816 A1* | 5/2012 | Smith | ............ | G06Q 50/24 |
| | | | | 705/3 |
| 2015/0149192 A1* | 5/2015 | Jester | ............ | G16H 40/20 |
| | | | | 705/2 |
| 2016/0117471 A1* | 4/2016 | Belt | ............ | G06F 19/3456 |
| | | | | 705/2 |
| 2017/0330174 A1* | 11/2017 | Demarinis | ............ | G06F 21/62 |

* cited by examiner

METHOD OF FACILITATING IMAGING STUDY INTERPRETATIONS BETWEEN HEALTHCARE FACILITIES AND PHYSICIANS

TECHNICAL FIELD

The present disclosure relates to facilitating communication between healthcare facilities and physicians and, more specifically, relates to a method and system of providing a decentralized and incentivized platform for enabling healthcare facilities to present requests for interpretation of imaging studies to a plurality of physicians and, depending upon parameters in the interpretation requests, allowing the healthcare facility to select a physician to provide their interpretation of the imaging studies.

BACKGROUND

Diagnostic imaging equipment is widely used for the purpose of diagnosing diseases and proposing treatment. There are over 20,000 CT scanners and MRI scanners in the United States and over 70,000 such scanners globally. It is also estimated that there are 500 healthcare facilities and 5,500 hospitals in the United States where these procedures are performed. In the U.S. alone, more than 700 million radiologic studies were conducted in 2016 that served as the foundation for diagnosing an illness and determining methods of treatment. Globally it is estimated that more than 2 billion radiology studies are performed. The professional radiology industry is a 20 billion dollar global industry and estimates predict that it will be growing 6-12% annually in the foreseeable future.

Imaging studies can be interpreted by radiologists on-site where images are generated or interpreted via a practice called teleradiology. Teleradiology refers to the practice of a radiologist interpreting medical images while not physically present in the location where the images are generated. Teleradiology can be practiced by internal/in-house radiologists/groups or outsourced to external radiologists/groups or teleradiology companies.

Performing and interpreting a diagnostic test is a complicated and dynamic process having numerous moving parts and involving multiple parties. A typical prior art process is illustrated in FIG. 1. Initially, the referring doctor issues an order to conduct the test based on an initial visit by the patient. The doctor evaluates numerous factors that will determine the medical necessity to perform the diagnostic test, including the patient's history, and indications and guidelines issued by the industry bodies. The order is then fulfilled on-site at the ordering physician's office or is transferred to a diagnostic imaging facility (typically a freestanding imaging center, hospital imaging department or mobile diagnostic company). Once the diagnostic test is performed by the imaging center, the images and accompanying documentation (imaging studies) including Digital Imaging and Communications (DICOM) data are transferred to the imaging center's local storage, which can be a picture archiving and communication system/radiology information system (PACS/RIS) system, where a radiologist (or cardiologist etc.) reviews the imaging studies and provides an interpretation in the form of a report. The report, which includes findings and diagnoses is saved in the patient's file and then delivered to the referring physician typically in electronic format, or can be made available online for download, or can be faxed. The referring physician can then validate the diagnosis by ordering additional diagnostic tests, prescribing non-invasive treatment and/or recommending an invasive procedure or surgery. The imaging center bills the insurance company for the performed procedure and the radiologist is paid a commission.

Several issues define the medical diagnostics field today. The increase in the aging population and broader availability and increased dependence on diagnostic imaging is contributing to the continued growth of imaging and the need for interpretation of these imaging studies. Advances in imaging technology have contributed to image complexity resulting in an increased number of imaging studies, especially for cross-sectional studies (e.g., CT, MRI, PET/CT, Breast Tomosynthesis, etc.). Also, referring doctors are demanding more detailed and specialized reports. These factors have contributed to increased interpretation times, and it has become typical for radiologists to work very long hours resulting in fatigue and burnout.

To respond to the increased demand for radiologists, costs of hiring a qualified radiologist are rising. Increasing the pressure is a strict turn-around time requirement that healthcare facilities and hospitals impose on the radiology companies, forcing the radiology companies to provide substantial additional capacity thus driving up interpretation costs. Combined with reduced payouts from insurance companies, this places a great deal of pressure on radiologists and leads to the second major issue: lack of quality with regard to study interpretation.

Errors in the proper application of medical diagnostic technology can lead to a misdiagnosis. Radiology is a complex field and frequently the studies are interpreted by radiologists who do not have appropriate training or experience. Many of these errors, missed-findings, misinterpretations and improper recommendations lead to delayed medical treatment, or no treatment at all, which may even lead to a poor outcome including death.

Various analytics have found that mistakes in study interpretation range anywhere from 10% to 30% of the studies performed. This staggering number affects the ability of physicians to provide proper treatment and leads to malpractice lawsuits and other financial penalties. To date, the only response from the industry was to perform quality assurance interpretation on exams to control the quality and identify mistakes. For example, the American College of Radiologists recommends that 5% of interpretations should be randomly checked by another radiologist. However, this is an expensive proposition and few companies follow these recommendations due to the prohibitive cost.

In the U.S. and some other countries, physicians must possess state licenses, be privileged at the facilities and credentialed with insurance plans in order to produce final reports. These requirements, including insurance credentialing, facility privileging and physician licensing, contribute to significant bottlenecks which exacerbate physician shortage. In order to provide interpretations each (tele)radiologist and other specialist must be licensed in the state where the patient is located and where he/she is located. The licensing process is slow and can take between 3 and 12 months or longer depending on the state and physician record. All hospitals and some private healthcare facilities require that physicians are privileged at their facilities, a process which can take between 1 and 12 months. Additionally, in order to provide final interpretations, physicians must be credentialed with numerous private or public insurance plans, a process which can also take up to 6 months depending on the insurance company. Thus, considering licensing, privileging and credentialing requirements, attempts to satisfy these requirements are a slow, manual process.

Finally, it is important to note that technology has always played an important role in medical diagnostics and helps increase doctor productivity and the accuracy of interpretation. Doctors are able to use advanced image reconstruction programs, computer analytics tools, voice recording and other advances in computers in their daily work. One of these technological advances is to use artificial intelligence ("AI") algorithms to help radiologists analyze imaging studies faster and more accurately. Such technology requires large sets of data to "train" AI programs on existing data sets, including interpretations and annotations of studies to "teach" the AI to recognize specific anomalies. However, to date, many of these datasets are difficult and expensive to obtain and are not freely available in the marketplace. Further, a critical shortage of qualified radiologists limits the availability of specialists for annotations. These factors severely limit the progress of AI companies, many of which have raised substantial amounts of money to bring their innovations to market.

In summary, the diagnostics industry is suffering from a critical shortage of specialists, rising interpretation costs, workflow inefficiencies, quality issues and lack of consolidated diagnostics data to advance AI analytics. What is therefore needed is a platform directed to solve the aforementioned issues and to help the industry to better serve patients at lower costs and with higher quality.

SUMMARY

According to one aspect of the present disclosure, a method for facilitating selection, by a healthcare facility, of a physician from a plurality of physicians to provide interpretation of an imaging study, is provided. The method includes receiving physician credentials from at least one physician, receiving, from the healthcare facility, an imaging study and a request for interpretation of the imaging study, the request including physician selection criteria, providing access to the imaging study and the request for interpretation to qualified physicians whose credentials match the physician selection criteria, receiving an interpretation of the imaging study from those qualified physicians that have accepted the request for interpretation, comparing the physician credentials to the physician selection criteria, and selecting an imaging study interpretation from the received imaging study interpretations based on the comparing of the physician credentials to the physician selection criteria.

According to another aspect, the present disclosure provides a non-transitory computer-readable storage medium having stored therein instructions which, when executed by a processor, cause the processor to perform operations including provide access to an imaging study and request for interpretation of the imaging study received from a healthcare facility to qualified physicians whose credentials match physician selection criteria received from the healthcare facility, compare the physician credentials to the physician selection criteria, and select an imaging study interpretation from imaging study interpretations received from those qualified physicians that have accepted the request for interpretation, the selecting based on the comparing of the physician credentials to the physician selection criteria.

DETAILED DESCRIPTION OF EXEMPLARY EMBODIMENTS

Blockchains are decentralized, peer-to-peer networked databases that can store and authenticate a ledger of assets and asset transactions. One benefit of blockchain technology is that transactions can occur without a third-party intermediary. Instead, transactions are validated by consensus. Blockchain technology provides the underlying platform for the issuance and redemption of crypto-tokens as well as an environment for the operation of smart contracts. Crypto-tokens can take a myriad of forms to represent units of value, rights, privileges, and/or access and be traded among interested parties. Smart contracts are computer programs designed to act as self-executing contracts that implement aspects of a transaction where the terms of the agreement between buyer and seller are directly written into lines of software code. The code and the agreements contained therein exist across a distributed, decentralized blockchain network. Beyond just transferring value from one place to another, smart contracts can access and transfer a variety of information depending upon predetermined conditions.

The present disclosure provides a platform that stores imaging data, as well as physicians' credentials in a format that is readily available for other entities to gain secure access. Using blockchain technology, the present disclosure provides a smart contracts concept, which allows instantaneous payment to providers and the issuing of reports to the requestors.

The embodiments disclosed herein refer to communication and the transfer of information between multiple entities including computers at healthcare facilities, computers at a control center, computers at physicians' offices, and computers at an Artificial Intelligence ("AI") company. These entities will be discussed in greater detail below. Further, although in one embodiment the physician can be a radiologist, the term "physician" shall be broadly construed throughout this disclosure to include any type of medical specialist that is capable of interpreting imaging studies, i.e., CT scan, MRI, PET/CT, Breast Tomosynthesis, or other types of imaging studies, such as cardiologists, dermatologists, pathologists, etc.

Figure 1:
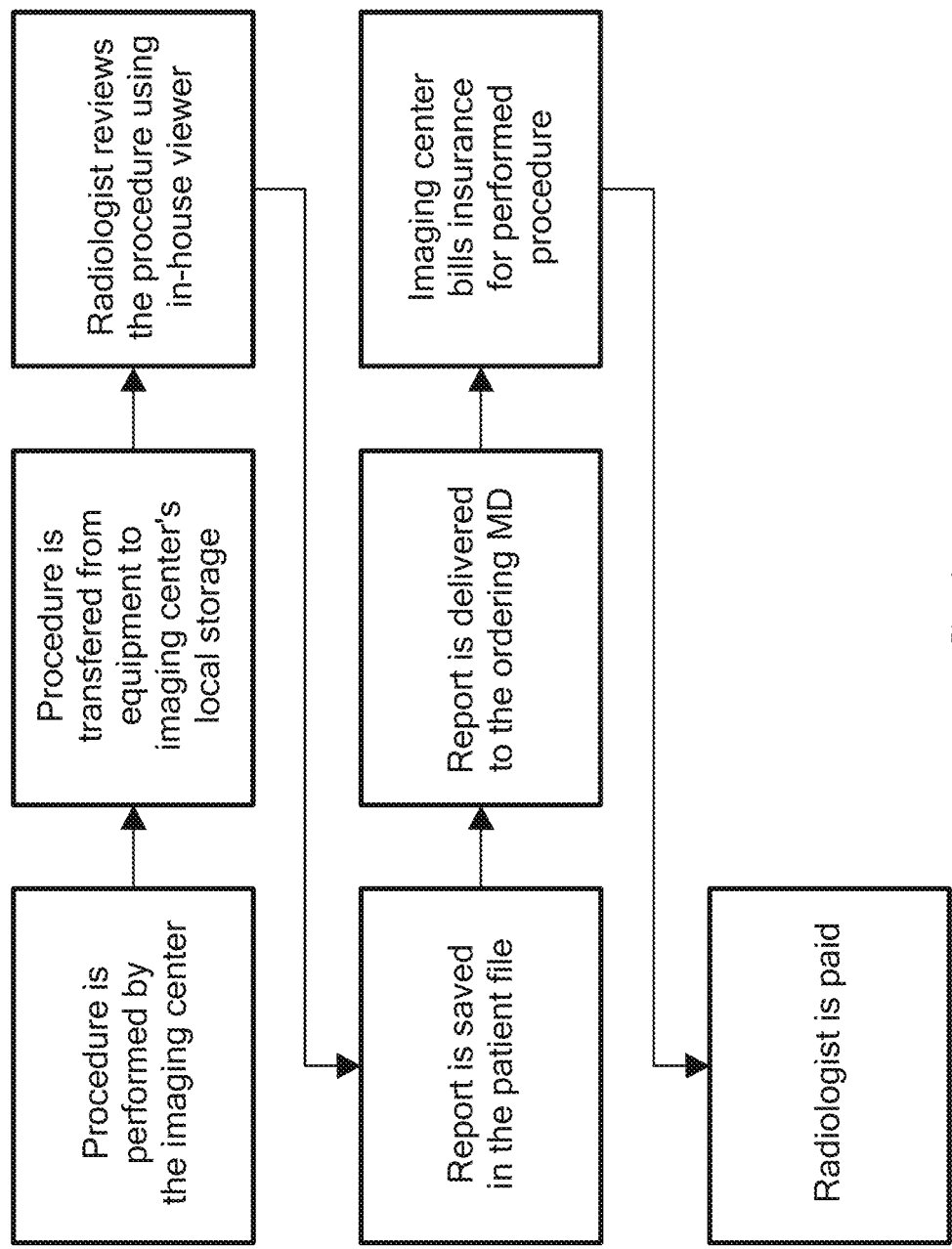
FIG. 1 is a flow diagram illustrating imaging study interpretation methods of the prior art.
Figure 2:
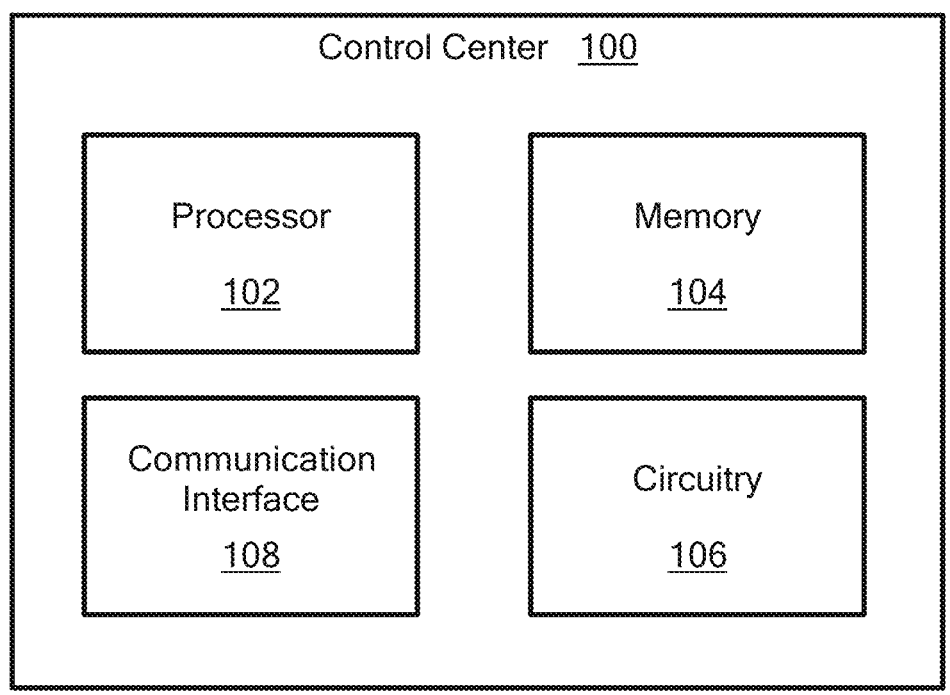
FIG. 2 is a block diagram of a control center operable to perform embodiments of the present disclosure.

Referring now to FIG. 2, an exemplary control center 100 of the present disclosure is shown. In one embodiment, control center 100 is a facility that includes a computer such as a server which includes a traditional processor 102, a memory 104, processing circuitry 106, and a communication interface 108. Processing circuitry 106 may include integrated circuitry for processing and/or control, e.g., one or more processors and/or processor cores and/or FPGAs (Field Programmable Gate Array) and/or ASICs (Application Specific Integrated Circuitry). The processing circuitry 106 may include and/or be connected to and/or be configured for accessing (e.g., writing to and/or reading from) the memory 104, which may comprise any kind of volatile and/or non-volatile memory, e.g., cache and/or buffer memory and/or RAM (Random Access Memory) and/or ROM (Read-Only Memory) and/or optical memory and/or EPROM (Erasable Programmable Read-Only Memory). Such memory 104 may be configured to store code executable by control circuitry and/or other data, e.g., data pertaining to communication, e.g., configuration and/or address data of nodes, etc. The processing circuitry 106 may be configured to control any of the methods described herein and/or to cause such methods to be performed, e.g., by the processor 102. Corresponding instructions may be stored in the memory 104, which may be readable and/or readably connected to the processing circuitry 106. In other words, the processing circuitry 106 may include a controller, which may comprise a microprocessor and/or microcontroller and/or FPGA (Field-Programmable Gate Array) device and/or ASIC (Application Specific Integrated Circuit) device. It may be considered that the processing circuitry 106 includes or may be connected or connectable to memory 104, which may be configured to be accessible for reading and/or writing by the controller and/or processing circuitry 106.

Figure 3:
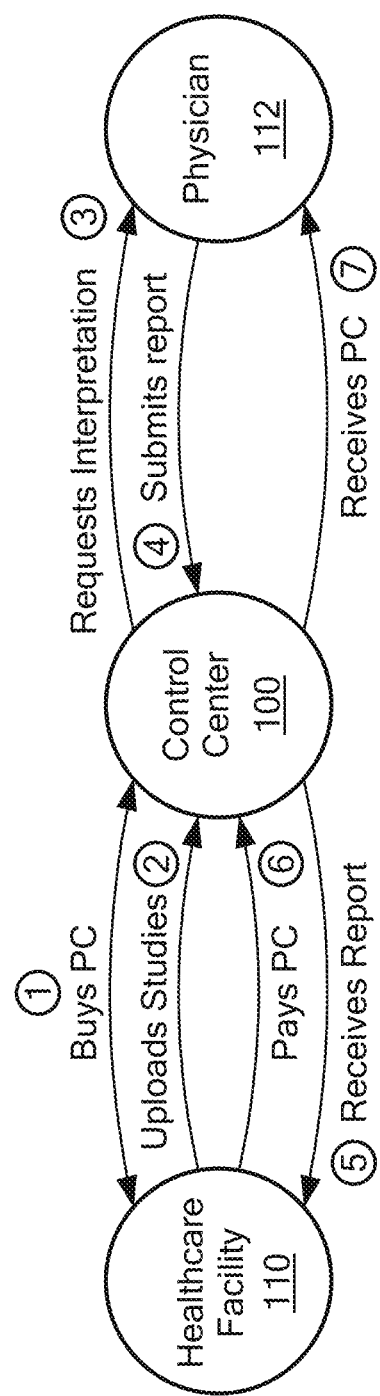
FIG. 3 is a diagram illustrating steps taken by the control center in order to facilitate the exchange of imaging study and imaging study interpretation reports between a healthcare facility and physician in accordance with embodiments of the present disclosure.

Referring to FIG. 3, control center 100 (also referred to herein as "platform") controls the communication and exchange of information, between computers at one or more healthcare facilities, collectively referred to as "healthcare facility" 110, and computers at one or more physician offices, collectively referred to as "physician" 112. Healthcare facility 110 can be any type of facility that engages in healthcare services. This may include imaging facilities that produce scanned images for cross-sectional studies (e.g., CT, MRI, PET/CT, Breast Tomosynthesis, etc.). Specifically, and as will be explained in greater detail below, control center 100 receives imaging studies, which are one or more images and which may include accompanying notes or documentation from the healthcare facility 110, that have been created by healthcare facility 110 along with requests from healthcare facility 110 for a physician 112 to examine and interpret (or annotate) the imaging studies. Qualified physicians 112 then interpret the imaging studies and provide annotated imaging study reports to control center 100, which then provides access to the reports to the requesting healthcare facility 110.

In one embodiment of the present disclosure, one or more healthcare facilities 110 register with control center 100. When healthcare facilities 110 register with control center 100, they create an account and purchase payment credits (indicated as step 1 in FIG. 3), giving the healthcare facilities 110 the ability to upload imaging studies and order interpretations of the imaging studies that control center 100 will help facilitate (indicated as step 2 in FIG. 3). The imaging studies can be uploaded directly from the healthcare facility's internal system, or manually from workstations. Once the imaging studies are uploaded, control center 100 creates a request for interpretation (indicated as step 3 in FIG. 3) that includes parameters for selection of the physician 112 that will be performing the interpretation.

Physicians 112, like healthcare facilities 110, also register with control center 100, submit their credentials and wait to receive requests for interpretation from healthcare facilities 110 via control center 100. In one embodiment, control center 100 also provides a credential validation feature, where an independent third party may validate the credentials of participating physicians 112, including licensing and board certifications and warrant their authenticity.

Once the imaging study is received from the healthcare facility 110, control center 100 creates a request for interpretation, records the request in a blockchain database, and "freezes" fees in a digital wallet created for the requesting healthcare facility 110. Control center 110, via its communication interface 108, forwards the interpretation request to those physicians 112 that have registered with the platform and that have qualifications that match the criteria specified by the requesting healthcare facility 110. Thus, when healthcare facility 110 sends a request for interpretation of an imaging study to control center 100, the request may include certain physician criteria. Such criteria might be, for example, the state that the physician 112 is licensed in, priority, i.e., whether the physician can supply an imaging study interpretation by a certain date, insurance credentialing, the subspecialty of the physician 112, price, and other information specified by the healthcare facility 110. Once one or more physicians 112 accept the request for interpretation of the imaging study, the request becomes unavailable to other physicians 112 (i.e., those that have not accepted the request for interpretation) and the accepting physicians begin their interpretation of the imaging study.

The selected physician 112 interprets the imaging study and submits a report, to control center 100, that includes the physician's comments, annotations, and interpretations of the imaging study (indicated as step 4 in FIG. 3). Control center 100 sends the report to the requesting healthcare facility 110 (indicated as step 5 in FIG. 3). Healthcare facility 110 then pays for the report in the form of payment credits (indicated as step 6 in FIG. 3), and, in turn, the physician 112 that interpreted the imaging study is paid from their efforts in the form of payment credits (indicated as step 7 in FIG. 3).

Control center 100 controls the receipt of payment from healthcare facilities 110 when the requesting imaging enter 110 receives an interpretation of its imaging study and the corresponding payment to the physician 112 that interpreted the imaging study via the use of a blockchain contract or "smart" contract. The rules of a blockchain contract or "smart" contract governing the interpretation and conditions of payment can include several additional parameters. For example, in one embodiment, such rules might specify the type of interpretation needed (e.g., draft, preliminary, or final), a requirement for double-reading, a second opinion, multiple-reading (also known as crowd-reading or consensus reading) or some other type of advanced agreements that are designed to increase imaging study interpretation quality.

For example, in one embodiment, healthcare facility 110 can ask for only a draft interpretation from a plurality of qualified physicians 112. In one embodiment, draft reads can be performed by any physician 112. These physicians 112 do not have to be privileged, credentialed or licensed and can prepare draft reads anonymously. The reports created are unofficial opinions and do not become part of official medical record. In another embodiment, preliminary reads may be requested. Preliminary reads are performed by physicians 112 who are privileged at the facilities and licensed in the state where the patient and physician 112 reside at the time of interpretation. These physicians 112 do not have to be credentialed with specific insurance plans. In this case, a physician 112 who is credentialed with the specific insurance plan must review the imaging studies and finalize the report. Preliminary reports become part of official medical record.

Final reads are performed by physicians 112 who are privileged, licensed and credentialed with an approved insurance plans and licensed in the state where the patient and the physician 112 reside at the time of imaging study interpretation. These physicians 112 can review the imaging studies and give the draft or preliminary report a final read and then prepare a finalized report, which becomes part of the official medical record. Healthcare facility 110 can review the received draft, preliminary or final reports, and either except one of them or reject them all in which case healthcare facility 110 submits another request which control center 100 can send to another physician 112 or group of physicians 112. In another embodiment, healthcare facility 110 can, with its request for imaging study interpretation that it sends to control center 100, include the requirement that the interpretation report prepared by physician 112 be read by another physician or physicians 112, i.e., a double-reading or a second opinion.

In another embodiment, the request for interpretation of the imaging study includes a requirement for consensus or "crowd reading." Crowd reads are performed by two or more physicians 112 when such a service is requested in order to provide extra assurance of a proper and accurate study of the imaging studies in the case of, for example, complex studies. A consensus is then calculated and proceeds are distributed based on optimal interpretation. There are two types of crowd reading using smart contracts. In a blind crowd reading, multiple physicians 112 provide independent interpretations of the imaging study. A smart contract executes and determines how payment among the reviewing physicians 112 is to be distributed. In one embodiment, the final report that is prepared is an integrated merged report and is based on a highest probability consensus. Highest probability consensus could be, as an example, if ten physicians 112 contribute reports, and nine are in agreement, but one differs, the opinion of the nine physicians 112 will be used. The fee is divided amongst all participating physicians 112 based on detail and correct interpretation. The fee is equally divided if all participating physicians 112 are in agreement and provide a detailed and error free report. If a final read is required, the last, finalizing physician 112 receives additional payment for the final report.

In another embodiment, an iterative crowd reading is requested, where a first qualified available physician 112 (i.e., in a first-come-first-serve scenario) provides an original interpretation of the imaging study. A second qualified available physician 112 reviews the original report of the first physician 112. If there is consensus, i.e., no editing needed, the second physician 112 receives a fee for proofreading of the original interpretation. If editing is needed, the second physician 112 receives a larger fee which is subtracted from the fee of the first physician 112. A third qualified available physician 112 then reviews the second report (from the second physician) and if there is a consensus, i.e., no editing needed, the third physician 112 receives a fee for proofreading. If editing is needed, the third physician 112 receives a larger fee which is subtracted from the fee of the first two physicians. This iterative process can continue depending upon the number of reviewing physicians 112. A smart contract executes after the last physician 112 completes their report and the fee is divided based on contribution of each physician 112 that contributed. For example, assuming the first physician 112 generates a report which does not need to be edited, the first physician 112 receives 50% of the total fee to generate the report and a 50% fee is equally divided by all participating physicians 112 for imaging study review. If the original reports need to be corrected, then a 50% report fee is fairly redistributed. If a final read is required, the last finalizing physician 112 receives an additional payment for the final report. The 50% scenario is exemplary only and any percentage arrangement is within the scope of the present disclosure.

When physician 112 completes the interpretation of the imaging study and uploads the report (containing the interpretation) to a computer, i.e., a server of the control center 100, the report becomes available to healthcare facility 110 and healthcare facility 110 can review the report and either accept it or reject it. If healthcare facility 110 report accepts the report, the smart contract executes and payment, in the form of payment credits is transferred to the wallet of physician 112 that supplied the report. Control center 100 keeps the fees in a digital wallet for that particular physician 112 for further distribution to token holders at the specified time. If healthcare facility 110 rejects the report, the healthcare facility 110 provides the reason for the rejection and submits a request for corrections. All communications between healthcare facility 110 and physician 112 go through control center 100 which uploads and makes available these communications to healthcare facility 110, participating physicians 112, and, in some embodiments, to others, such as, other non-participating physicians or a quality assurance panel, which could be a group of expert specialists.

Physician 112 complies with the request from healthcare facility 110, re-submits their report, and resubmits a request to control center 100 for payment. If healthcare facility 110 is still not satisfied with the report and the healthcare facility 110 and physician 112 cannot come to an agreement, the parties can ask for dispute resolution by requesting a crowd-read and a dispute resolution panel. This dispute resolution panel is assembled randomly from participating physicians 112 that will render a final interpretation. The physicians 112 on the resolution panel could be, for example, select physicians that meet a certain level of expertise for that particular imaging study. For example, if the imaging study relates to a brain MRI, the physicians on the panel could be expert radiologists that possess a certificate of additional qualifications ("CAQ") in the field of neuroradiology. Payment for the work of the panel will be taken from the fees accumulating by control center 100 for this transaction on a digital dedicated wallet. Alternatively, imaging facility 110 may decide to have the report to be interpreted by a different physician 112, for example, a dedicated specialist. Thus, if the case is rejected, healthcare facility 110 may request that the study is (i) re-interpreted by the same physician 112 or request that the same physician 112 edit the report; (ii) interpreted by a different physician 112; or interpreted by a group, i.e., a panel of physicians 112.

Figure 4:
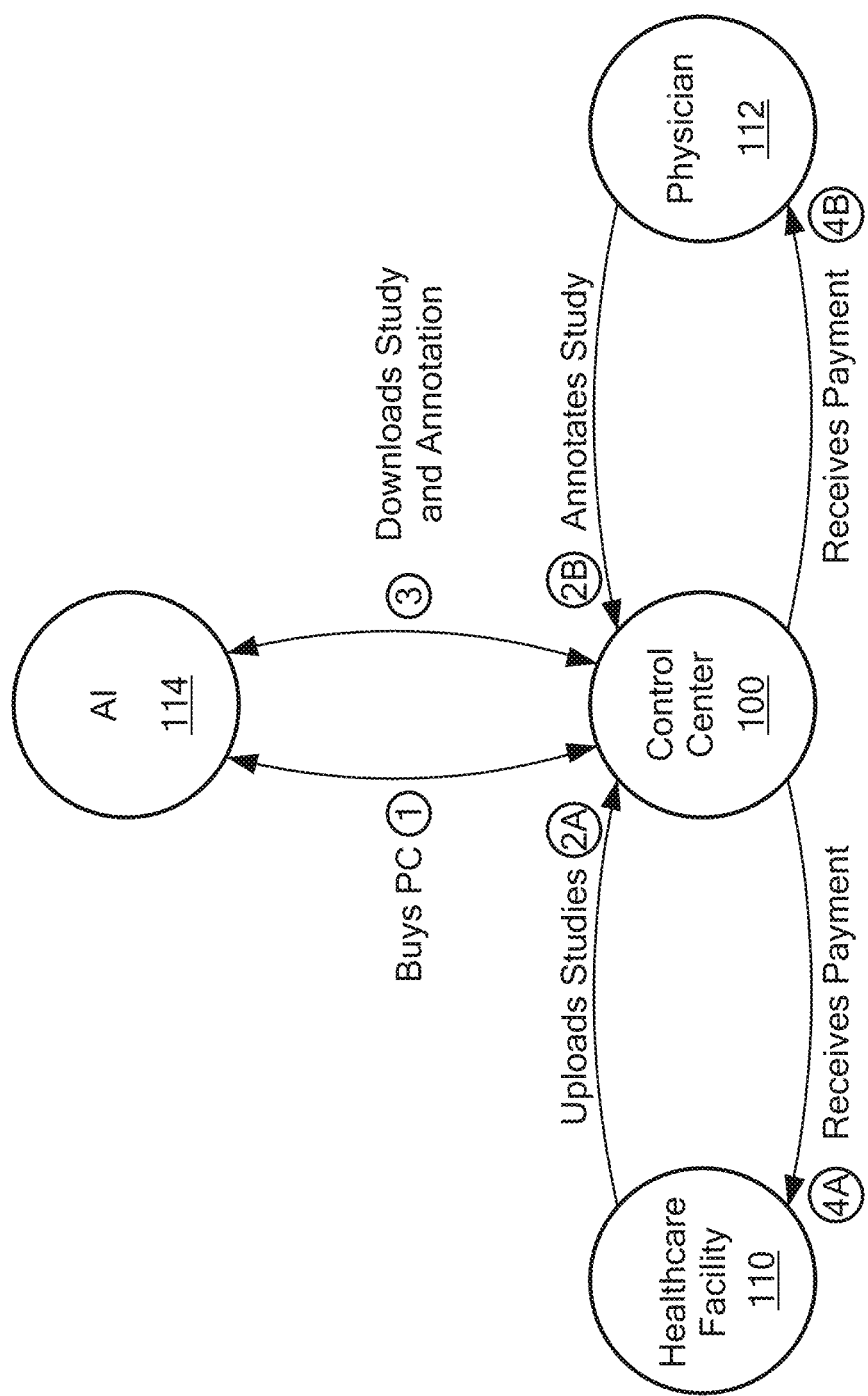
FIG. 4 is a diagram illustrating steps taken by the control center in order to facilitate the exchange of imaging studies and image interpretation reports between a healthcare facility, physicians, and AI companies, in accordance with embodiments of the present disclosure.

Referring now to FIG. 4, an alternate embodiment of the present disclosure is shown. In this embodiment, the workflow relates to accumulating data (imaging studies, reports and annotations) between healthcare facilities 110 and physicians 112 and the content is made available to any number of artificial intelligence (AI) companies 114 (collectively referred to herein as "AI company 114"). AI company 114 focuses on data mining and building smart algorithms to aid those in need, i.e., physicians such as radiologists, neurologists, cardiologists, etc., in preparing their final annotated reports. AI company 114 uses AI algorithms to help physicians 112 analyze imaging studies faster and more accurately.

In order for AI company 114 to participate, it will also need to register with and have a digital wallet created by control center 100 and purchase at least one security token from control center 100. To get access to imaging studies and other imaging data, AI company 114 can purchase the required number of payment credits from control center 100, which will be placed in a digital wallet for AI company 114. Upon placing a request to access data, the payments credits for AI company 114 become frozen in its digital wallet and are transferred to recipients' (healthcare facility's 110 and physician's 112) wallets upon the AI company's acceptance of the imaging studies provided by healthcare facility 110 and imaging study annotations provided by physicians 112. Payment credits are distributed to owners of the imaging studies (typically healthcare facilities 110), authors of annotations and reports (typically physicians 112), as well as to control center 100, where the credits can be distributed into other accounts, for example, into the support budget, cost accounts and into a special system wallet for dividends and rebates.

In step 1 of the process depicted in FIG. 4, one or more AI companies 114 purchases payment credits from control center 100. As in the earlier embodiment, healthcare facility 110 uploads or otherwise sends imaging studies (step 2A in FIG. 4) and a request for annotation to control center 100 which makes the imaging studies and request for annotation available to participating physicians 112. The selected physician 112 annotates the study and forwards it to control center 100 (step 2B in FIG. 4). Control center 100 forwards the annotated report to AI company 114 (step 3 in FIG. 4). In the context of this disclosure, the term "forwarding" an imaging study, a study, or a report, to another entity, can be defined as sending the document from one computer to another, or uploading the document on a server thereby making the imaging study, or report available for access by other entities. Healthcare facility 110 and physician 112 each receive payment (steps 4A and 4B in FIG. 4) in the manner described below.

When submitting the imaging study to control center 100, the healthcare facility 110 can specify that it desires to store the study for further monetization and the physician 112 can also annotate the study in a specific fashion, annotating pathologies and providing information about the pathologies. The study marked in a blockchain database is "owned" by the healthcare facility 110 that submitted the imaging study and the physician 112 that submitted the annotated report and is anonymized to comply with privacy and legal requirements. AI company 114 can request to select a study or collection of studies matching certain criteria from a database associated with control center 100 (i.e., either a database located at the same facility as control center 100 or at a remote data base that control center 100 can access) and downloads the study or collection of studies for analysis. When AI company 114 downloads the study, it makes a payment to control center 100 and this payment is divided between the healthcare facility 110 (in payment tokens) that provided the imaging studies and physicians 112 (in payment tokens) that provided the annotations. Smart contract governs these transactions. Control center 100 retains its own fee, for example, for further distribution.

AI company 114 uses an AI algorithm to generate a report. A smart contract executes and when the algorithm is ready for production, one or both of the healthcare facility 110 and the physicians 112 can use the algorithm to generate reports. AI company 114 receives payment each time the algorithm is used, while, in one embodiment, control center 100 also retains a commission each time the algorithm is used. In another embodiment, control center 100 can receive further commission each time the algorithm is used, once the algorithm has been approved for commercial use. A first available qualified physician 112 reviews the AI generated report. A smart contract executes. If there is a consensus (no editing needed) the first reviewing physician 112 receives a certain number of tokens as payment for proofreading. If editing is needed, the first reviewing/editing physician 112 receives a certain number of tokens and a certain number of corresponding tokens are subtracted from the digital wallet of AI company 114. Therefore, the better and more accurate algorithms get higher reimbursement.

According to embodiments of the present disclosure, control center 100 can derive profits from the exchange of information, i.e., imaging studies, physician-generated annotated imaging study reports, and AI-generated reports, in a variety of ways. One way is for control center 100 to receive payment for processing transactions for healthcare facilities 110. For each transaction, control center 100 charges a predetermined amount. Many healthcare facilities 100 working with in-house providers (whether reading the imaging studies onsite or via teleradiology) wish to improve efficiency of imaging transactions by integrating with the solution provided by the present disclosure. In-house providers can include any physicians 112 with which healthcare facilities 110 have existing and established relationships and may include current independent physicians, i.e., radiologists, teleradiologists, cardiologists and other specialists as well as physician groups and teleradiology companies. For these types of transactions, in one embodiment, control center 100 charges healthcare facilities 110 a fee of X % of the transaction value, e.g., 5%, payable to control center 100 in payment credits. In one embodiment, the fee can vary depending upon the type of imaging study, i.e., CT, XRay, positron emission tomography (PET) scan, etc. In a further embodiment, if healthcare facility 110 agrees to make the studies available to be annotated and to be sold to AI companies 114, the fee charged by control center 100 will be reduced to an amount less than X %.

A second method in which control center 100 can receive payment as an intermediary according to embodiments of the present disclosure, is for brokering interactions between imaging facilities 110 and outsourced physicians 112. With a physician shortage crisis, many imaging facilities 110 are not able to hire and staff the appropriate number of physicians 112. Imaging facility 110 or other that are requesting interpretation of imaging studies pay a "per click" transaction fee to control center 100 for interpretations and control center 100 keeps some portion of it as fees. Depending upon the type of read requested by the healthcare facility 110, e.g., draft, preliminary, final, or crowd reading, the pricing differs.

During certain hours of the day (typically deep night, i.e., the "graveyard shift"), certain weekend hours, and holidays, there is traditionally a significant increased demand for services due to severe physician shortages. To prevent these shortages and volume surges during high traffic times, price increases may be instituted by control center 100 in order to balance demand for services and physician supply. The price increase can based on predetermined formulas and markups can vary, i.e., from 10% to 100%. For example, during national holidays the price increase may double (100% increase). During times of modest increased demand, the price may increase 10-50% in order to drive more physicians 112 during those hours.

A third way that control center 100 can receive payment is by being a broker between AI company 114 and imaging facilities 110/physicians 112 by providing access to data and physicians 112. AI company 114 desires to access control center 100 in order to purchase access to anonymized imaging studies, interpretations and annotations. Every imaging study uploaded to control center 100 will be marked with the digital wallet of its owner, i.e., the healthcare facility 110 that has uploaded the imaging study. Each physician report and annotation will be also marked with its owner, i.e., the physician 112 that performed the evaluation, i.e., annotation of the imaging study and prepared the report. Control center 100 will allow transfer of such ownership to other participants. For example, if an AI company 114 wants to perform a specific type of annotation of the imaging studies, AI company 114 can request work to be done, pay for it and retain its ownership.

A fourth way that control center 100 can receive payment is when AI company 114 offers its algorithms for use and purchase by healthcare facilities 110 and physicians 112. For example, when AI companies 114 register on the platform they select a price model they plan to work under as well as indicating specific imaging studies and pathologies their algorithms are capable of analyzing. When the imaging studies are uploaded to control center 100 by the healthcare facility 110, the customer sees all available algorithms that they can use to assist in interpreting specific imaging studies. The healthcare facility 110 can select an algorithm and purchase it, or can recommend specific algorithms to interpreting physicians 112. The physician that accepts can chose to use this algorithm, or, if no recommendation was done, physician 112 can select an appropriate algorithm and purchase it. Control center 100 receives a portion of this fee and distributes the balance to AI company 114.

In one embodiment, the present disclosure operates with a token model architecture whereby control center 100 will issue a security token giving its holders the right to dividends generated by control center 100 and certain voting rights to ensure proper governance of the platform. In one embodiment, issuance of the security token is limited by an initially issued amount, and new tokens will not be issued. In one embodiment, the security token is mandatory to own in order to get access to the functionality of the platform, so the token can be sold or issued to investors, participants in the platform, or to anyone. The participants will also receive rebates based on amount of work done on the system and their token holding. Payments on the platform are conducted using payment credits, as described above. These payment credits may be implemented as security tokens, but are the only method used by the platform for payments, rebates and dividends.

Healthcare Facility Participation

Healthcare facilities 110 can participate on the platform by purchasing payment credits and at least one security token to be placed into its digital wallet. Such purchase can be done using fiat (credit card or bank transfer) or a selected crypto payment (i.e., BITCOIN or ETHEREUM). The purchased credits will be placed into a digital wallet that is created for the healthcare facility 110 during registration on the platform. Once credits have been purchased, healthcare facility 110 can upload the imaging studies and create a request for interpretation to control center 100. Upon creation of the request, the required number of payment credits will be frozen in the healthcare facility's wallet while awaiting results of interpretation. When results (i.e., a report) from physician 112 are received by control center 100 and accessed or sent to healthcare facility 110, and healthcare facility 110 accepts the report, payment credits are transferred to the recipients' digital wallets, i.e., the physicians 112 that performed interpretation, various cost accounts (i.e., imaging study storage costs), platform support budgets and special system wallets that will keep credits designated for dividends and rebates.

The digital wallet will also be used to receive dividends and rebates owed to the healthcare facility 110 at the end of the dividend period. These payments will be executed as transfer of payment credits calculated proportionately to the security token ownership (dividends) and according to a rebate table, taking into account the amount of work uploaded to control center 100 by that particular healthcare facility 110.

Physician Participation

In order for physician 112 to participate in the platform, the physician 112 will need to purchase at least one security token that will be placed into their digital wallet created during registration. This digital wallet will receive payment for interpretations performed on the platform and also dividends payable according to the number of security tokens owned by the physician 112. The payment credits kept in this digital wallet can be redeemed for cash or fiat at any point in time and these credits will also be used to fund deposit for dispute resolution in case healthcare facility 110 is not satisfied with the work of the physician 112 that submitted the annotated imaging study report.

AI Company Participation

In order for AI company 114 to participate in the platform, the AI company 114 will also need to register with the platform, create a digital wallet and purchase at least one security token with control center 100. To obtain access to imaging studies and other data, AI company 114 will need to purchase a predetermined number of payment credits, which will be placed in its digital wallet. Upon placing a request with control center 100 to access data or a request to perform certain work, the credits associated with the requesting AI company 114 become frozen in their digital wallet and are transferred to the recipients' wallets (the physician 112 that perform the annotation of the imaging studies (upon acceptance of their work). Credits are distributed to owners of the imaging studies (typically healthcare facilities 110), authors of annotations and reports (typically physicians 112), as well as into various support budgets, cost accounts and special system wallets for dividends and rebates.

In another embodiment, in order to attract a larger number of imaging facilities 110 to join the platform, submit imaging studies, and request interpretations, the platform will distribute rebates to healthcare facilities 110, reducing their cost of interpretations proportionately to the work they route to control center 100 and the amount of security tokens held by the healthcare facilities 110. In a non-limiting exemplary embodiment, an healthcare facility 110 that submits between 1,000 and 5,000 imaging studies/requests for interpretations per month can receive a rebate of 1% if the healthcare facility 110 has purchased less than 1,000 tokens, a rebate of 1.5% if the healthcare facility 110 has between 1,000 and 10,000 tokens, a 2% rebate if the healthcare facility 110 has between 10,000 and 100,000 tokens, and a 2.5% rebate if the healthcare facility 110 has greater than 100,000 tokens. Similarly, an healthcare facility 110 that submits between 5,001 and 10,000 imaging studies/requests for interpretations per month can receive a rebate of 1.5% if the healthcare facility 110 has purchased less than 1,000 tokens, a rebate of 2% if the healthcare facility 110 has between 1,000 and 10,000 tokens, a 2.5% rebate if the healthcare facility 110 has between 10,000 and 100,000 tokens, and a 3% rebate if the healthcare facility 110 has greater than 100,000 tokens.

The percentages can increase if, for example, the healthcare facility 110 submits more imaging studies and requests for interpretation per month.

In one embodiment, each healthcare facility 110 and physician 112 receives a predetermined number of tokens upon registering with the platform and also (for healthcare facilities 110) receives a predetermined number of tokens upon submitting a certain number of imaging study interpretation requests and (for physicians 112) receive a predetermined number of tokens upon completing a certain number of interpretations.

Dispute Resolution

As discussed above, on certain occasions, healthcare facilities 110 (or their customers, e.g., referring doctors, patients, etc.) may not be satisfied with reports submitted by physician 112. In these instances, healthcare facilities 110 have an option to reject the physician report and submit a request that physician 112 amend the report. In the event that the physician's amended report is not satisfactory to healthcare facility 110, healthcare facility 110 has an option to either send this case to another physician 112 or to raise a dispute and assign the case to a crowd-read dispute resolution panel for a second opinion. The dispute resolution panel consists of multiple physicians, selected randomly, that will provide their unbiased opinion on whether the interpretation that is being disputed was performed properly. Control center 100 coordinates payment to the panel from its cost account and from the payment credit deposits made by both participants, i.e., the healthcare facility 110 and the physician 112. Upon resolution of the dispute, if the dispute resolution panel determines that the disputed physician report was correct, payment credits frozen on the healthcare facility's digital wallet are transferred to the physician 112. If the panel determines that the disputed physician report was incorrect, the frozen payment credits are returned to the digital wallet of the healthcare facility 110.

Payment Credit Redemption

Payment credits are used as the method of monetary exchange on the platform. In one embodiment, each payment credit is equal to one U.S. dollar. Credits are issued by the platform at the moment of registration and are backed by cryptocurrency and fiat placed in the segregated accounts. At any point in time the amount of credits issued is precisely equal to the amount of cash and cryptocurrency in those accounts. At any point in time any participant holding payment credits can elect to redeem the credits and receive an equal amount of cash or fiat transferred to them. Upon redemption, the credits are eliminated or "burned", keeping the balance between the money in the bank and the amount of credits outstanding. Credits are used by the platform to pay fees and dividends and can only be exchanged between registered participants in the platform. Credits have no value outside of the system and are non-transferrable.

Figure 5:
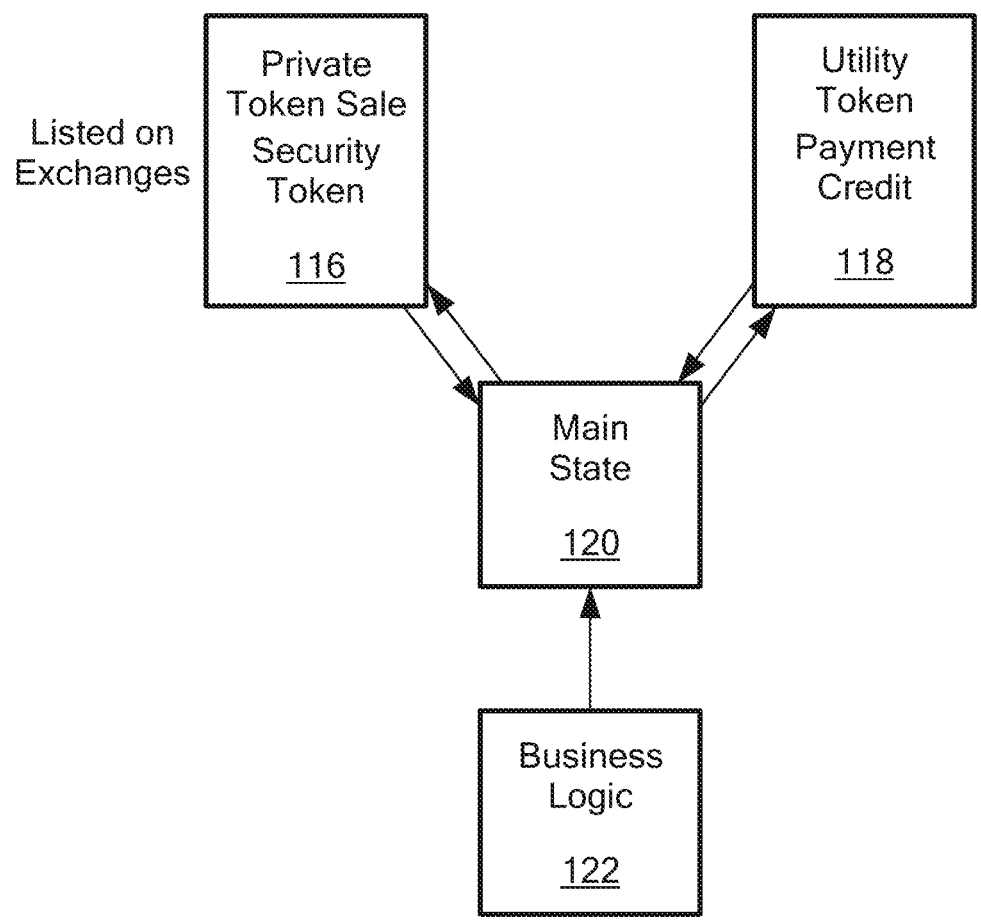
FIG. 5 is a block diagram illustrating the smart contracts layer in accordance with embodiments of the present disclosure.

Referring to FIG. 5, a block diagram is shown, illustrating an exemplary embodiment of the stack architecture of the present disclosure. The control center 100 of the present disclosure includes the use of smart contracts to provide transparency in distributions from monetary transactions and to reduce transaction costs associated with contracting. In one embodiment, an ETHEREUM blockchain is used as a decentralized application (dAPP) layer, where smart contracts are used to execute commands and retrieve information from the blockchain. The present disclosure also uses web portals to provide easy access to all the aspects of the blockchain and to create additional services for all the parties using control center 100. Any web technologies may be used including, for example, ANGULAR, NodeJS, and Amazon cloud services, etc.

In one embodiment, the smart contracts layer includes four different contracts, where one contract without state will be changed during the platform development to avoid migrations risks. Referring to FIG. 5, security tokens 116 as referred to herein can be purchased by investors and represent stakeholders share in platform revenues. In one embodiment, ERC20 can be used as the token standard using ETHEREUM blockchain. Ownership of security tokens 116 is necessary to operate on the platform and the address of the security token owner's digital wallet address will be used to distribute rebates and dividends. In one embodiment, this contract will not be changed without consent of the token holders. In one embodiment, this token can be listed on exchanges and permitted to be traded between investors.

Payment credits 118 as referred to herein, are constant-value stable coin tokens. In one embodiment, ERC20 can be used as the token standard using ETHEREUM blockchain. Payment credit 118 tokens can be used for all payments for services performed on the platform 100, as well as payment of dividends and rebates. In one embodiment, the token value is guaranteed by money in an audited bank account and it will be minted or burned based on purchase or sale of payment credits by platform participants. In one embodiment, the contract governing payment credit tokens 118 cannot be altered.

Main state 120 is the entity that keeps the state about users, examinations and their status. Main state 120 interacts with security tokens 116 and payment credit tokens 118. In one embodiment, the main state 120 is not changed, but if there is a need to expand the state, one or more additional main states will be created alongside the main state 120. For example, after the creation of a smart contract, the main state is fixed. If additional data elements need to be added, an additional main state repository can be created to keep the additional data elements.

Business logic 122 represents hardware and software that doesn't maintain any state but has knowledge about all platform business processes. Business logic 122 interacts with main state 120 and is constantly evolving.

Each party using control center 100, i.e., healthcare facilities 110, physicians 112 and AI companies 114 may use web portals to access control center 100. Web portals for healthcare facilities 110 allows the healthcare facilities 1110 several ways to upload imaging studies; i.e., via existing medical systems (e.g., using portal widgets), via an existing PACS Server, or via manual upload (i.e., using the platform portal). In this fashion, the healthcare facility 110 via control center 100 can control the life-cycle of an imaging study examination procedure, beginning with the sending of the imaging studies by healthcare facility 110 to physicians 112 via control center 100, receiving and reviewing the annotated report from the physicians 112, making the annotated reports available to healthcare facilities 110 and evaluating and rating the physician's performance.

Web portals for physicians 112 gives physicians 112 the opportunity to accept requests for imaging study annotations, study and annotate the imaging studies via any medical imaging study viewer (for example but not limited to a DICOM imaging study viewer), and upload/write reports for the interpreted examination of the imaging study, which is returned, via control center 100, to the requesting healthcare facility 110 for evaluation.

Web portals for AI companies 114 allows AI companies 114 to search through collected databases (e.g., DICOM databases) and upload collections of imaging studies and imaging study reports for review, such as neural network learning purposes.

Physician Ratings

Physicians 112 are rated for each report they generate. In a non-limiting example, a scale of 1 to 10 is used (where 1 is the lowest score and 10 the highest), where if the physician 112 generates a perfect report which is detailed and error free then the physician 112 receives a perfect score of 10 for that particular report. Lack of important details and various types of errors in the report will affect the score. In one embodiment, different types of errors can affect the score differently, where the score can be reduced more for more critical errors. Other factors that can be used to rate each physician 112 and factor into their score are their training, i.e., medical school, residency, and fellowship), their work experience, number of years in practice, medical malpractice history, etc.

Other factors can negative or positively affect the physician rating, such as customer satisfaction or dissatisfaction, etc. Physicians 112 have an incentive to preserve the highest score possible since customers (i.e., healthcare facilities 110) can set their threshold when selecting physicians 112 and requesting imaging study annotations (e.g., "select physicians having a rating of 7 or higher") and typically physicians 112 with higher scores acquire more tokens for each read. In one embodiment, physicians 112 having a score below a predetermined rating can be eliminated from control center 100.

Figure 6:
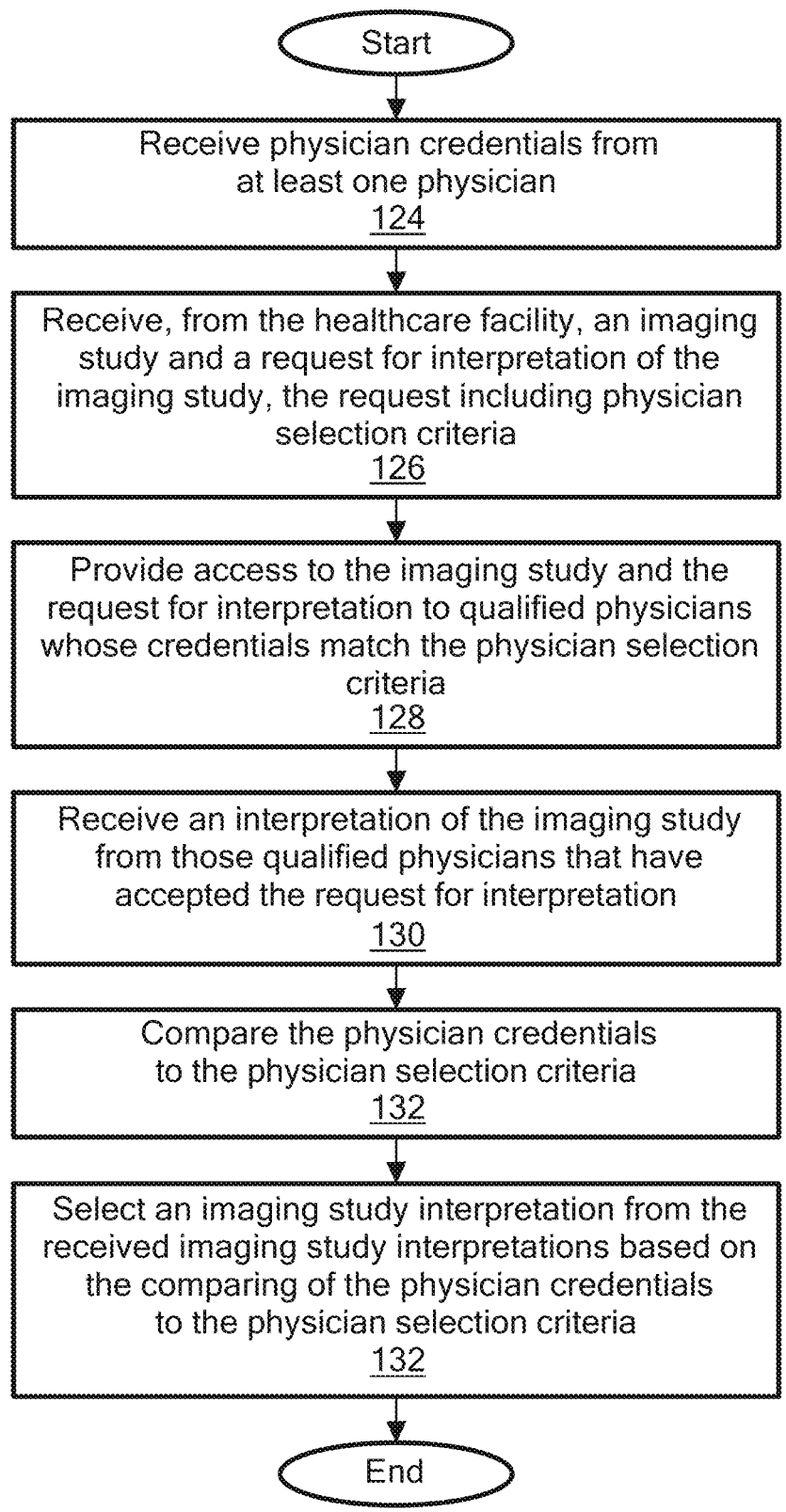
FIG. 6 is a flow diagram illustrating steps taken by the control center in order to select an imaging study interpretation in accordance with embodiments of the present disclosure.

FIG. 6 is a flowchart illustrating an exemplary method performed by control center 100, for facilitating selection, by an healthcare facility 110, of a physician 112 from a plurality of physicians 112 to provide interpretation of an imaging study. In one embodiment, the method includes receiving, by communication interface 108 of control center 100, physician credentials from at least one physician 112, (step 124); receiving, by communication interface 108, from healthcare facility 110, an imaging study and a request for interpretation of the imaging study, the request including physician selection criteria (step 126); providing access to the imaging study and the request for interpretation to qualified physicians 112 whose credentials match the physician selection criteria as determined by processor 102 (step 128); receiving, by communication interface 108, an interpretation of the imaging study from those qualified physicians 112 that have accepted the request for interpretation (step 130); comparing, by processor 102, the physician credentials to the physician selection criteria (step 132), and selecting, by processor 102, an imaging study interpretation from the received imaging study interpretations based on the comparing of the physician credentials to the physician selection criteria (step 134).

The selection of an imaging study interpretation from the received imaging study interpretations can be based on several criteria selected by the customer, i.e., healthcare facility 110. For example, processor 102 can select the imaging study interpretation based on the type of report required by healthcare facility 110, i.e., draft, preliminary, or final, and the modality of the report, i.e., solo, dual-read or crowd reads. Other criteria could be location, whether the physician 112 is U.S.-based, or based in a specific country, credentials, i.e., board certification, certificates of added qualifications (CAQs) and other special certifications, licensing (for final reports), physicians and report quality scores, and credentialing with insurance plans (final reads). The afore-mentioned criteria is not exhausted and the list of criteria is merely exemplary. The criteria used by healthcare facilities 110 is included in the annotation request sent to control center 100 or otherwise provided to control center in the physician selection process. This information can be stored in a database at control center 100 or in a remote database that can be accessed by processor 102 and circuitry 106 of control center 100 in order to select the imaging study interpretation that best matches the customer's, i.e., the healthcare facility's 110 criteria.

In another embodiment, the physician credentials are validated by a third party. In another embodiment, the method shown in FIG. 6 further includes the step of recording the request for interpretation in a blockchain database. In another embodiment, the physician selection criteria includes at least one of state of physician license, insurance company used by physician, modality of the requested report, physician rating, and the price for the physician's services.

In another embodiment, upon acceptance of the request for interpretation from qualified physicians 112, processor 102 makes the request inaccessible to other physicians 112. In another embodiment, the request for interpretation includes interpretation requirements, the interpretation requirements including at least one of a draft interpretation, a preliminary interpretation, a final interpretation, and a multiple-reading, i.e., crowd-reading requirement. In another embodiment, the method shown in FIG. 6 further includes, receiving, by communication interface 108, from the healthcare facility 110, an approval of the selected imaging study interpretation, deducting, by processor 102, fees from an electronic wallet of the healthcare facility 110, and depositing, by processor 102, fees into an electronic wallet of the qualified physician 112 whose imaging study interpretation was approved by the healthcare facility 110.

In another embodiment, the method further includes receiving, by communication interface 108, from the healthcare facility 110, a rejection of the selected imaging study interpretation, an explanation for the reasons of rejecting the imaging study interpretation, and a request from the healthcare facility 110 for resubmittal of a revised imaging study interpretation. In another embodiment, the method further includes receiving, by communication interface 108, from at least one of the healthcare facility 110 and the physician 112 that supplied the selected imaging study interpretation, a dispute resolution request to be performed by an independent dispute resolution panel.

In another embodiment, a blockchain contract governs the dispute resolution. In another embodiment, the method includes generating, by processor 102, a rating for each physician 112 that provides imaging study interpretations.

In another embodiment, the method further includes receiving, by communication interface 108, from the healthcare facility 110, a request that information related to the imaging study is stored in a blockchain database, the information including at least one of the imaging study, the imaging study interpretation, and annotations to the imaging study interpretation, providing third party access to the stored information, and upon a third party accessing the stored information, receiving, by communication interface 108, electronic payment from the third party and distributing at least a portion of the received electronic payment into respective blockchain wallets of the healthcare facility 110 and the physician 112 that supplied the accessed imaging study interpretation.

In another embodiment, the method further includes, issuing, by processor 102, at least one security token to the third party to enable the third party to access the stored information and receiving payment from the third party for the at least one security token. In another embodiment, the stored information is identified in a blockchain database as being owned by the requesting healthcare facility 110. In another embodiment, the method further includes, receiving, by communication interface 108, electronic payment from the healthcare facility 110 via a blockchain transaction for each request for interpretation of the imaging study. In another embodiment, the method further includes receiving, by communication interface 108, electronic payment from the qualified physician 112 that provided the interpretation of the imaging study via a blockchain transaction for each imaging study interpretation. In another embodiment, a blockchain contract governs all electronic payments concerning the imaging study and the imaging study interpretation.

In another embodiment, the method further includes issuing, by processor 102, at least one security token to the healthcare facility 110 and to the physician 112, the issued at least one security token to be placed in the corresponding electronic wallet of the healthcare facility 110 and physician 112, and receiving, by communication interface 108, payment for the issued at least one security token as a condition for registration.

In another embodiment, the method further includes providing incentives, by processor 102, for the healthcare facility 110 to provide requests for interpretation and for the physicians 112 to submit imaging study interpretations. In another embodiment, the incentives include issuing free security tokens upon registration of a healthcare facility 110 or a physician 112 and issuing free security tokens after a predetermined number of requests for interpretations by the healthcare facility 110 or imaging study interpretations by the physicians 112 have been received.

In another embodiment, the method includes providing, by processor 102, a mark-up of the payment received from the healthcare facility 110 during at least one predetermined time frame. In another embodiment, the qualified physicians 112 that interpret the imaging study receive payment credits for each interpreted imaging study. In another embodiment, the payment credits are exchangeable for security tokens. In another embodiment, the qualified physicians 112 outsource the imaging study interpretation to another physician 112, a digital wallet of the qualified physicians 112 being reduced, by processor 102, for each outsourced imaging study interpretation and a digital wallet of the other physician 112 performing the outsourced imaging study interpretation being increased, by processor 102, for each imaging study the other physician interprets.

In another embodiment, the method includes rating, by processor 102, each qualified physician 112 that as submitted at least one interpretation, the rating based on predetermined rating criteria. In another embodiment, receiving, by communication interface 108, from the healthcare facility 110, a preference indicator, the preference indicator indicating at least one of at least one physician 112 that the healthcare facility 110 prefers to receive interpretations from and at least one physician 112 that the healthcare facility 110 prefers to not to receive interpretations from.

The method shown in FIG. 6, and the embodiments described above, may be performed by processor 102 that is configured to execute computer program instructions from a computer program stored in memory 104 or another non-transitory computer-readable medium that is in, or is accessible to the processing circuitry 106.

For clarity of explanation, in some instances the present technology may be presented as including individual functional blocks including functional blocks comprising devices, device components, steps or routines in a method embodied in software, or combinations of hardware and software.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims. Moreover, claim language reciting "at least one of" a set indicates that one member of the set or multiple members of the set satisfy the claim.

What is claimed is:

1. A non-transitory computer-readable storage medium having stored therein instructions which, when executed by a processor, cause the processor to perform operations comprising:

record in a blockchain database an imaging study received from a healthcare facility and a request for interpretation of the imaging study received from the healthcare facility, the request for interpretation of the imaging study including a request for crowd reading, the crowd reading being an iterative crowd reading where a first qualified physician provides an original interpretation of the imaging study and receives an original interpretation fee, and if edits are required to the original imaging study interpretation, at least one additional qualified physician iteratively edits the original imaging study interpretation, each of the at least one additional qualified physician receiving a corresponding editing fee, the editing fee being deducted from at least the original interpretation fee until no further edits are needed, resulting in an iterative imaging study interpretation, the resulting imaging study interpretation forming the consensus imaging study interpretation;

provide access to the imaging study and the request for interpretation of the imaging study received from the healthcare facility to qualified physicians whose credentials match physician selection criteria received from the healthcare facility;

compare the physician credentials to the physician selection criteria;

select an imaging study interpretation from imaging study interpretations received from those qualified physicians that have accepted the request for interpretation, the selecting based on the comparing of the physician credentials to the physician selection criteria, the selected imaging study interpretation being a consensus imaging study interpretation, the consensus imaging study interpretation formed by calculating a consensus of the multiple physician interpretations of the imaging study;

record the selected imaging study interpretation in the blockchain database, the imaging study and the imaging study interpretation being anonymized;

manage all electronic payments concerning the imaging study and the imaging study interpretation using a blockchain contract;

wherein the processor is further operable to process an electronic payment to be sent to a third party entity that creates algorithms based on use of the algorithms in analyzing the imaging study, and wherein the electronic payment to the third party is based on each use of the algorithms.

2. The non-transitory computer-readable storage medium of claim 1, wherein the physician credentials are validated by a third party.

3. The non-transitory computer-readable storage medium of claim 1, wherein the physician selection criteria includes at least one of a state the physician is licensed in, an insurance company used by physician, modality of the physician's report, physician rating, and price for the physician's services.

4. The non-transitory computer-readable storage medium of claim 1, wherein upon acceptance of the request for interpretation from qualified physicians, the processor is further operable to make the request inaccessible to other physicians.

5. The non-transitory computer-readable storage medium of claim 1, wherein the request for interpretation comprises interpretation requirements, the interpretation requirements including at least one of a draft interpretation, a preliminary interpretation, a final interpretation, and a multiple-reading requirement.

6. The non-transitory computer-readable storage medium of claim 1, wherein upon receipt from the healthcare facility of an approval of the selected imaging study interpretation, the processor is further is configured to:
 deduct fees from an electronic wallet of the healthcare facility; and
 deposit fees into an electronic wallet of the qualified physician whose imaging study interpretation was approved by the healthcare facility.

7. The non-transitory computer-readable storage medium of claim 1, wherein the processor is further operable to process a rejection of the selected imaging study interpretation received from the healthcare facility, an explanation for the reasons of rejecting the imaging study interpretation, and a request from the healthcare facility for resubmittal of a revised imaging study interpretation.

8. The non-transitory computer-readable storage medium of claim 7, wherein the processor is further operable to process from at least one of the healthcare facility and the physician that supplied the selected imaging study interpretation, a received dispute resolution request to be performed by an independent dispute resolution panel.

9. The non-transitory computer-readable storage medium of claim 8, wherein the blockchain contract governs the dispute resolution.

10. The non-transitory computer-readable storage medium of claim 1, wherein the processor is further operable to generate a rating for each physician that provides imaging study interpretations.

11. The non-transitory computer-readable storage medium of claim 1, wherein upon receipt, from the healthcare facility, of a request that information related to the imaging study is stored in the blockchain database, the information including at least one of the imaging study, the imaging study interpretation and annotations to the imaging study interpretation, the processor is further operable to:
 provide third party access to the stored information;
 upon a third party accessing the stored information, process received electronic payment from the third party; and
 distribute at least a portion of the received electronic payment into respective blockchain wallets of the healthcare facility and the physician that supplied the accessed imaging study interpretation.

12. The non-transitory computer-readable storage medium of claim 11, wherein the processor is further configured to issue at least one security token to the third party to enable the third party to access the stored information and receiving payment from the third party for the at least one security token.

13. The non-transitory computer-readable storage medium of claim 11, wherein the stored information is identified in the blockchain database as being owned by the requesting healthcare facility.

14. The non-transitory computer-readable storage medium of claim 1, wherein the processor is further operable to process a received electronic payment from the healthcare facility via a blockchain transaction for each request for interpretation of the imaging study.

15. The non-transitory computer-readable storage medium of claim 1, wherein the processor is further operable to process a received electronic payment from the qualified physician that provided the interpretation of the imaging study via a blockchain transaction for each imaging study interpretation.

16. The non-transitory computer-readable storage medium of claim 1, wherein the processor is further operable to:
 issue at least one security token to the healthcare facility and to the physician, the issued at least one security token to be placed in the corresponding electronic wallet of the healthcare facility and physician; and
 process a received payment for the issued at least one security token as a condition for registration.

17. The non-transitory computer-readable storage medium of claim 1, wherein the incentives include issuing free security tokens upon registration of an healthcare facility or a physician and issuing free security tokens after a predetermined number of requests for interpretations by the healthcare facility or imaging study interpretations by the physicians have been received.

18. The non-transitory computer-readable storage medium of claim 15, wherein the processor is further operable to comprising provide a mark-up of the payment received from the healthcare facility during at least one predetermined time frame.

19. The non-transitory computer-readable storage medium of claim 1, wherein the qualified physicians that interpret the imaging study receive payment credits for each interpreted imaging study.

20. The non-transitory computer-readable storage medium of claim 19, wherein the payment credits are exchangeable for security tokens.

21. The non-transitory computer-readable storage medium of claim 1, wherein the qualified physicians outsource the imaging study interpretation to another physician, a digital wallet of the qualified physicians being reduced for each outsourced imaging study interpretation and a digital wallet of the other physician performing the outsourced imaging study interpretation being increased for each imaging study the other physician interprets.

22. The non-transitory computer-readable storage medium of claim 1, wherein the processor is further operable to rate each qualified physician that as submitted at least one interpretation, the rating based on predetermined rating criteria.

23. The non-transitory computer-readable storage medium of claim 1, wherein the processor is further operable to process a preference indicator received from the healthcare facility, the preference indicator indicating at least one of at least one physician that the healthcare facility prefers to receive interpretations from and at least one physician that the healthcare facility prefers to not to receive interpretations from.

24. The non-transitory computer-readable storage medium of claim 1, wherein the received electronic payment is based on each time the third party entity accesses at least one of the imaging study and the imaging study interpretation.

25. The non-transitory computer-readable storage medium of claim 1, wherein the received electronic payment is based on each time the third party offers its algorithms for at least one of use and purchase to at least one of the healthcare facility and the physician.

26. The non-transitory computer-readable storage medium of claim 1, wherein the request for interpretation comprises interpretation requirements, the interpretation requirements including a multiple-reading requirement.

27. The non-transitory computer-readable storage medium of claim 1, wherein the crowd reading is a blind crowd reading where two or more qualified physicians provide independent interpretations of the imaging study, and the consensus imaging study interpretation is based on the provided independent interpretations of the imaging study.

28. A non-transitory computer-readable storage medium having stored therein instructions which, when executed by a processor, cause the processor to perform operations comprising:
    record in a blockchain database an imaging study received from a healthcare facility and a request for interpretation of the imaging study received from the healthcare facility, the request for interpretation of the imaging study including a request for crowd reading, the crowd reading being an iterative crowd reading where a first qualified physician provides an original interpretation of the imaging study and receives an original interpretation fee, and if edits are required to the original imaging study interpretation, at least one additional qualified physician iteratively edits the original imaging study interpretation, each of the at least one additional qualified physician receiving a corresponding editing fee, the editing fee being deducted from at least the original interpretation fee until no further edits are needed, resulting in an iterative imaging study interpretation, the resulting imaging study interpretation forming the consensus imaging study interpretation;
    provide access to the imaging study and the request for interpretation of the imaging study received from the healthcare facility to qualified physicians whose credentials match physician selection criteria received from the healthcare facility;
    compare the physician credentials to the physician selection criteria;
    select an imaging study interpretation from imaging study interpretations received from those qualified physicians that have accepted the request for interpretation, the selecting based on the comparing of the physician credentials to the physician selection criteria, the selected imaging study interpretation being a consensus imaging study interpretation, the consensus imaging study interpretation formed by calculating a consensus of the multiple physician interpretations of the imaging study;
    record the selected imaging study interpretation in the blockchain database, the imaging study and the imaging study interpretation being anonymized;
    manage all electronic payments concerning the imaging study and the imaging study interpretation using a blockchain contract;
    wherein upon receipt from the healthcare facility of an approval of the selected imaging study interpretation, the processor is further is configured to:
    deduct fees from an electronic wallet of the healthcare facility;
    deposit fees into an electronic wallet of the qualified physician whose imaging study interpretation was approved by the healthcare facility; and
    process, from at least one of the healthcare facility and the physician that supplied the selected imaging study interpretation, a received dispute resolution request to be performed by an independent dispute resolution panel to evaluate a disputed physician report, wherein upon resolution of the dispute, if the panel determines that the disputed physician report was correct, payment credits frozen on the healthcare facility's electronic wallet are transferred to the physician and if the panel determines that the disputed physician report was incorrect, the frozen payment credits are returned to the electronic wallet of the healthcare facility.

\* \* \* \* \*